United States Patent [19]

Bruson et al.

[11] 3,936,498

[45] *Feb. 3, 1976

[54] DETERGENT BUILDERS

[75] Inventors: Herman A. Bruson, Woodridge, Conn.; Henry Gould, Houston, Tex.

[73] Assignee: Olin Corporation, New Haven, Conn.

[*] Notice: The portion of the term of this patent subsequent to Oct. 2, 1990, has been disclaimed.

[22] Filed: Oct. 15, 1973

[21] Appl. No.: 406,325

Related U.S. Application Data

[62] Division of Ser. No. 183,277, Sept. 23, 1971, Pat. No. 3,767,598.

[52] U.S. Cl............ 260/537 R; 252/89 R; 252/135; 252/524; 252/525; 252/526; 252/527; 252/531; 252/532; 252/534; 252/535; 252/542; 252/544; 252/545; 252/546; 252/550; 252/551; 252/553; 252/554; 252/557; 252/558; 260/247.2 R; 260/293.88; 260/465 F; 260/465 H; 260/465.1; 260/465.6; 260/465.8 R; 260/501.1
[51] Int. Cl.²........................................ C07C 55/24
[58] Field of Search...... 260/247.2 R, 537 R, 501.1, 260/293.88

[56] References Cited
UNITED STATES PATENTS

| | | | |
|---|---|---|---|
| 2,329,433 | 9/1943 | Bruson | 260/537 R |
| 2,342,606 | 2/1944 | Bruson | 260/537 R |
| 2,456,517 | 12/1948 | Ladd et al. | 260/537 R |
| 3,661,787 | 5/1972 | Brown | 260/537 R |
| 3,763,231 | 10/1973 | Bruson et al. | 260/537 R |

*Primary Examiner*—Vivian Garner
*Attorney, Agent, or Firm*—Kenneth P. Glynn

[57] ABSTRACT

A detergent builder composition having the formula:

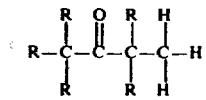

wherein R is —CH$_2$—CH$_2$—COOX, X being a member selected from the class consisting of hydrogen, alkali metals, ammonium and substituted ammonium.

3 Claims, No Drawings

DETERGENT BUILDERS

CROSS REFERENCE TO RELATED APPLICATIONS

This is a division of application Ser. No. 183,277, filed Sept. 23, 1971, now U.S. Pat. No. 3,767,598.

BACKGROUND OF THE INVENTION

1. Summary of the Invention

The present invention relates to a detergent builder composition having the formula:

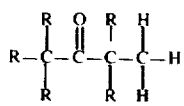

wherein R is —$CH_2$—$CH_2$—COOX, X being a member selected from the class consisting of hydrogen, alkali metals, ammonium and substituted ammonium.

2. Description of the Prior Art

The broad concept of "built" detergent compositions has been known for some time and encompasses the capability possessed by certain substances of substantially improving the effectiveness of detergent compounds. The improved or enhanced result as evidenced by a washed article appearing cleaner and brighter is generally characterized as the "builder" effect. Compounds which perform in this manner are called builders. The improved performance attributed to the builder is manifested in a variety of ways. Among the ways with respect to which builders are thought to have useful effects are such factors as stabilization of suspended solid soils, emulsification of soils, the surface activity in an aqueous detergent solution, the solubilization of water-insoluble materials, foaming or suds producing characteristics of the washing solutions, peptization of soil agglomerates, neutralization of acid soils and the like, in addition to the sequestration of mineral constituents present in the washing solution. The term "detergent" is used in a general sense and is intended to embrace both cleaning and whiteness maintenance properties. Built detergent compostions prepared specifically for laundering the wide range of natural and synthetic fabrics commonly in use today are termed "heavy-duty" detergents. Such compositions rely for their effectiveness, in part, on a relatively high proportion of builder materials being present in the composition.

The nature of the building action, while quite widely recognized in the literature is not completely understood. There does appear to be some connection between the ability of a builder to soften water which is used to make up the washing solution and the improved result in detergency obtained when the builder is used. However, not all materials which act to sequester hardness-imparting calcium and magnesium ions perform satisfactorily as builders. No general basis has been found or is known either as regards physical properties or in chemical structure upon which one can predict with any degree of accuracy the performance of chemicals as detergent builders. Further, useful building actions with the most effective builders can be noted both above and below the point at which the builder is present in the washing solution in stoichiometric proportions to the hardness in water.

Building effects in detergents have been noted in connection with various inorganic alkaline salts such as alkali metal carbonates, bicarbonates, phosphates, polyphosphates and solicates. Similar building properties have also been noted in connection with certain organic salts such as alkali metal, potassium ethylenediaminetetraacetate, sodium and potassium N-(2-hydroxyethyl)ethylenediaminetriacetate, sodium and potassium nitrilotriacetate, and sodium, potassium and triethanolammonium-N-(2-hydroxyethyl)-nitrilodiacetate. Alkali metal salts of phytic acid have also been utilized to some degree as organic builders in detergent formulations.

In recent years, the detergent industry has become concerned about water pollution caused by phosphates. The use of these builders is being discouraged or prohibited by law in order to curtail the growth of algae in rivers, lakes and streams where the residues from household and industrial detergents can collect, causing ecological damage by maintaining an active growth of algae that normally require phosphate ions for metabolism and survival.

Cyanoethylation of various ketones with acrylonitrile has produced a variety of compositions. For example, it has been disclosed in U.S. Pat. No. 2,386,736, entitled "Cyanoethylation of Ketones," that acrylonitrile can be reacted in the presence of alkaline condensing agent with a ketone having an active methyl, methylene, or methenyl group immediately adjacent to the carbonyl group. The reaction results in a beta-cyanoethyl radical being attached to the carbon atom adjacent to the carbonyl group. Ketones which can be reacted in this manner include methyl ethyl ketone, phenoxyacetone, cyanoacetone, ethoxyacetone, acetophenone, p-methyl-acetophenone, acetyl-p-cymene, and the like. The polycarboxylic acid salt is then produced by saponification of hydrolysis.

It has now been surprisingly discovered that organic pentacarboxylic acids and water-soluble salts thereof prepared from cyanoethylated methyl ethyl ketone which is subsequently hydrolyzed, possesses extraordinary builder properties for a variety of cynthetic detergents: for example, the long chain alkyl benzene sulfonate type, such as sodium isododecyl benzene sulfonate and sodium alkylaryl sulfonate. These carboxylic acids and salts do not contain phosphorus or nitrogen which can act to enhance and maintain the growth of algae.

It is therefore an object of the present invention to provide a new and improved class of detergent builder materials.

It is a further object of the present invention to provide a new detergent composition.

It is a further object of the present invention to provide a new process for preparing a detergent composition.

Other objects and advantages of the present invention will be readily apparent to those skilled in the art from a reading of the specification and claims which follow.

DESCRIPTION OF THE PREFERRED EMBODIMENTS

The polycarboxylic acids and water-soluble salts thereof used in the present invention may be prepared by reacting methyl ethyl ketone in the presence of a strongly basic alkaline catalyst with sufficient acrylonitrile to introduce 5 beta-cyanoethyl groups into the methyl ethyl ketone molecule. Catalysts useful for this purpose are the alkali metals and their oxides, hydroxides, alkoxides, and hydrides, as well as strongly basic quaternary ammonium hydroxides and alkoxides. One or several of these materials may be suspended or dissolved in methyl ethyl ketone or in a solution of methyl ethyl ketone in an enert liquid which is less reactive than the reacting methyl ethyl ketone, such as tertiary butyl alcohol. The quality of strongly basic alkaline catalyst necessary for the reaction is between about 0.1% and 2.0% on the combined weight of the reactants. Preferably, about 1.0% is utilized.

The amount of acrylonitrile necessary to react with methyl ethyl ketone to produce 5 beta-cyanoethyl groups on the methyl ethyl ketone molecule will, of course, vary with the temperature and time of the reaction, as well as the selected solvent system and catalyst. However, good yields of 5 beta-cyanoethylated methyl ethyl ketone can be successfully obtained by utilizing about 280 grams of acrylonitrile dissolved in about 120 grams of tertiary butyl alcohol, for each gram mole of methyl ethyl ketone.

The reaction between methyl ethyl ketone and acrylonitrile takes place readily at temperatures during the first half of the reaction from about 25°C to about 35°C, preferably at 30°C. During the second half of the reaction, temperatures between about 50°C and 65°C are utilized, preferably 60°C. The reaction has been found to be exothermal so that cooling, at least during the initial part of the reaction, may be advantageous in order to control the vigor of the reaction and to prevent undesired polymerization or side reactions.

The reaction which occurs is:

can be neutralized with sodium hydroxide. Of the remaining two carboxyl groups, one each can be neutralized with potassium hydroxide and lithium hydroxide. These ratios can be varied to suit relevant conditions of crystallinity, hygroscopicity, and ease of spray drying, to meet the specific needs of various powdered, packaged detergents to give a readily flowable, non-caking, non-hygroscopic, white crystalline product. For most commercial, powdered, synthetic detergents, the pentasodium salt of pentacarboxyethyl methyl ethyl ketone, is preferred because of low cost and efficiency. However, other water-soluble salts may also be used. For example, sodium, potassium, lithium, ammonium, ethanolammonium, diethanolammonium, triethanolammonium, cyclohexylammonium, morpholinium, piperidinium, hydrazinium, benzyl ammonium, and the like, may also be successfully used.

Many varieties of synthetic detergents may be built with the builder of the present invention. For example, anionic detergents may be successfully utilized. These detergents are water-soluble salts, especially the alkali metal salts of sulfuric reaction products having in their molecular structure an alkyl radical containing from about 8 to about 22 carbon atoms and a radical selected from the class consisting of sulfonic acid and sulfuric acid ester radicals. Among the particular materials which can be used are: (1) the sodium alkyl sulfates, particularly those obtained by sulfating high carbon alcohols produced by reducing glycerides of tallow or coconut oil, (2) sodium or potassium alkylbenzenesulfonates in which the alkyl group contains about $C_9$ to about $C_{18}$, (3) sodium alkylpolyethersulfonates, espe-

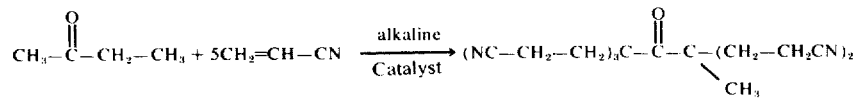

These cyanoethylation products are then hydrolyzed to the corresponding polycarboxylic acid salts by reacting with, for example, an aqueous alkali metal hydroxide, such as a sodium or potassium hydroxide solution to "split off" ammonia as completely as possible, giving a water-soluble salt. For example, in the case of the preparation of the sodium salt the reaction would be as follows:

cially those ethers of the higher alcohols derived from tallow and coconut oil, (4) sodium coconut oil fatty acid monoglyceride sulfates and sulfonates, (5) sodium or potassium salts of sulfuric acid esters of the reaction product of 1 mole of a higher fatty alcohol and about 1 to 6 moles of ethylene oxide, (6) sodium or potassium salts of alkylphenol polyoxyalkylene ether sulfate with about 1 to 10 units of alkylene oxide per molecule and

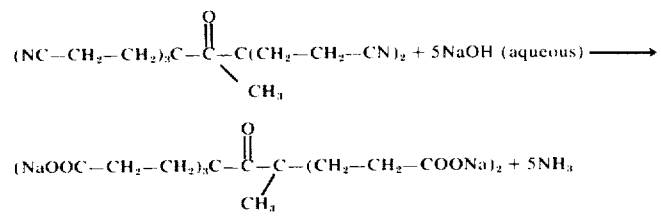

Any free alkali can be neutralized with strong acids such as sulfuric or hydrochloric acid since the presence of minor amounts of alkali metal sulfates or chlorides in the dried finished product is tolerated in the detergent composition itself. The solvent may also be evaporated off to leave behind the non-volatile salt of the polycarboxylic acid.

The water-soluble alkali metal salts of the polycarboxylic acids prepared as above described can, if desired, contain more than one species of alkali metal cation. For example, three of the five carboxyl groups in which the alkyl radicals contain about 9 to about 18 carbon atoms, (7) the reaction product of fatty acids esterified with isethionic acid and neutralized with sodium hydroxide, where, for example, the fatty acids are derived from coconut oil, and (8) sodium or potassium salts of fatty acid amides of taurine in which the fatty acids are derived from coconut oil or the like. These detergent compounds can be formulated into a variety of forms such as granular, flake, liquid, powder and tablet forms.

Generally speaking, when preparing either granular or liquid detergent formulations, about 5% to about 50% of the total active formulation may consist of the present builder. Under normal circumstances, about 10% of our builder has been found to be preferred. However, the exact amount of the builder composition of the present invention utilized will vary depending on the base detergent formulation and the particular commercial application at hand.

Our builder composition has been found to have particular utility in liquid detergents. Liquid detergents have posed especially perplexing and difficult problems for the detergent formulators, mainly because of solubility and stability factors in aqueous mediums. It is well known that although sodium tripolyphosphate is effective in granular detergents, it is not satisfactory in liquid formulations because of conversion to orthophosphate. In view of the increasing acceptance by the industry of liquid detergents it is a very significant contribution of the present invention that an improved built liquid detergent product is made possible that will provide detergency levels far superior to a sodium tripolyphosphate built liquid product in a liquid formulation.

Most of the built liquid detergents available are either water based or have a mixture of water and alcohol as the liquid base. Our detergent builder composition may be satisfactorily utilized in these bases.

A detergent formulation containing our builder composition may contain a variety of miscellaneous additives which may make the finished product more effective and commercially attractive. For example, a soluble sodium carboxymethylcellulose may be added in minor amounts to inhibit soil redeposition. A tarnish inhibitor such as benzotriazole or ethylenethiourea may be added in minor amounts. Fluorescence, perfume, coloring compounds, and optical brightening agents may be frequently desirable. An alkaline material or alkali such as sodium or potassium hydroxide may be added in minor amounts for pH adjustment. Additionally, moisture and brightening agents such as sodium sulfate and sodium carbonate may also be added. Other minor additives may also include corrosion and scale inhibitors and hydrotropic agents to promote homogeneity at lower temperatures.

The following examples further illustrate the novel qualities of the present invention:

EXAMPLE I

The present example illustrates the preparation of the present builder composition. Into a one liter 3-neck flask fitted with a stirrer, thermometer, funnel and reflux condenser, was added a solution of 40 grams of tertiary butyl alcohol and 36 grams methyl ethyl ketone. While stirring, 0.5 grams of reagent potassium hydroxide pellets were added. To this solution was added dropwise a solution of 60 grams tertiary butyl alcohol and 140 grams of acrylonitrile. Intermittent water bath cooling was required because of an observed vigorous exotherm. 50% of the acrylonitrile solution was first added within 35 minutes at a temperature of about 25°C–35°C. After the acrylonitrile addition, the reaction was "aged" for 45 minutes. 0.5 grams of potassium hydroxide pellets was then added as additional catalyst. The remaining acrylonitrile solution was then added during a 1 hour period. The reaction temperature rose to 48°C. The reaction batch was then permitted to "age" for 2½ hours at about 50°C to 60°C.

The solvent and volatiles were distilled under vacuum to a terminal 115°C pot temperature and 3mm pressure and the residue was hydrolyzed by adding 150 grams of sodium hydroxide dissolved in 325 grams of water. The batch was heated to reflux at 95°C at which point vigorous ammonia evolution was noted. The reflux was continued for about 3 hours until the ammonia in the overhead was negligible. Reflux was then continued for 11 additional hours to complete the hydrolysis with intermittent distillate removal. The excess caustic was neutralized with concentrated hydrochloric acid. The resulting product was 39% active sodium salt of 1, 1, 1, 3, 3 pentacarboxyethyl 3 methyl acetone.

EXAMPLE II

Standard Tergotometer tests were made to determine the soil removal effectiveness of a representative laundry detergent composition containing a control formulation and 10% of the builder composition of the present invention in a similar formulation. This test is one commonly used in the industry and is detailed in "Proposed Method for Measuring Soil Removal and Whiteness Retention of Fabrics," published by the American Society for Testing and Materials, February, 1969. This method provides a means of measuring the ability of detergents to remove artifical soil from fabric and prevent its redeposition on clean fabric. A laboratory-scale agitator-type washing machine is utilized, together with a reflectometer which is calibrated by means of standard vitreous enamel plaques having reflectance in the range of the fabric sample being measured. The washer is operated at a suitable fixed speed which is recorded with test results. After washing, the sample material is damp dried between clean toweling and then ironed flat between two pieces of clean white cotton sheeting. The reflectance readings are then determined. The test builder of the present invention was a sample of the sodium salt made as in Example I. The detergent compositions were as follows:

| | Control (% by wt.) | Test Formula (% by wt.) |
|---|---|---|
| Polycarboxylic builder | — | 10.0 |
| Carboxymethyl cellulose | 1.0 | 1.0 |
| Sodium silicate | 7.0 | 7.0 |
| Sodium sulfate | 76.0 | 66.0 |
| Linear sodium alkylaryl sulfonate | 16.0 | 16.0 |

Each sample was tested at a dilution of 0.25% in water having a hardness rating of 15 grains per gallon. Detergency was measured as the increase in diffuse of reflectance accomplished after the laundering of the following three different soiled cloths:

1. Test fabric soiled cotton, wash and were finish
2. ACH 115 soiled cotton*
3. U.S. Testing Soiled Cotton

* Supplied by ACH Fabric Service, Inc., Boston, Mass.

The calculation of the improvement in reflectance was made as follows:

Percent improvement in reflectance = $[(A-B)/(C-B)] \times 100$ where:

A = average reflectance of 16 soiled swatches after washing

B = average reflectance of 16 soiled swatches before washing, and

C = average reflectance of 4 unsoiled swatches before washing.

To assure the presence of the correct amount of each formula ingredient in the wash solution, dilute aqueous solutions of both samples were prepared and added on an aliquot basis to the Tergotometer beaker.

The Tergotometer test was made in accordance with the following test conditions:

| | |
|---|---|
| Amount of solution/vessel | 1 liter |
| Temperature | 125°F ± 1° |
| Speed of agitation | 150 cycles/minute |
| Water hardness | 15 grains/gallon |
| Concentration of formulated detergent | 0.25% |
| Wash time | 15 minutes |
| Rinse | 2 five minute cycles |

The results of soil removal tests are as follows:

Table 2A

| | Average increase in Diffuse Reflectance | | | |
|---|---|---|---|---|
| Builder | ACH 115 Cotton | U.S. Testing Cotton | Testing Fabric Cotton | Total Gain |
| Control | 32.6 | 5.4 | 15.5 | 58.5 |
| Polycarboxylic acid salt | 35.1 | 6.6 | 17.6 | 59.3 |

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What we claim is:

1. A detergent builder composition having the formula:

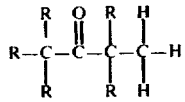

wherein R is —$CH_2$—$CH_2$—COOX, X being a member selected from the class consisting of hydrogen, alkali metals, and ammonium.

2. The builder composition of claim 1 wherein R is: —$CH_2$—$CH_2$—COONa.

3. A detergent builder composition having the formula:

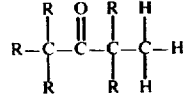

wherein R is —$CH_2$—$CH_2$—COOX, X being a member selected from the class consisting of hydrogen, alkali metals, ammonium and mixtures thereof.

* * * * *